United States Patent [19]

Gaertner

[11] 3,991,095

[45] Nov. 9, 1976

[54] N-THIOLCARBONYL DERIVATIVES OF N-PHOSPHONOMETHYLGLYCINE

[75] Inventor: Van R. Gaertner, Ballwin, Mo.

[73] Assignee: Monsanto Company, St. Louis, Mo.

[22] Filed: Dec. 29, 1975

[21] Appl. No.: 644,784

[52] U.S. Cl. ............................. 260/455 A; 71/87
[51] Int. Cl.² ................................. C07C 155/02
[58] Field of Search .................... 71/86; 260/45 SA

[56] References Cited
UNITED STATES PATENTS

| | | |
|---|---|---|
| 3,455,675 | 4/1969 | Irani ........................................ 71/86 |
| 3,799,758 | 3/1974 | Franz ....................................... 71/86 |
| 3,835,000 | 9/1974 | Frazier et al. ........................... 71/86 |
| 3,853,530 | 12/1974 | Franz ....................................... 71/86 |

*Primary Examiner*—Lewis Gotts
*Assistant Examiner*—D. R. Phillips
*Attorney, Agent, or Firm*—Arnold H. Cole; Donald W. Peterson

[57] ABSTRACT

Certain N-thiolcarbonyl derivatives of N-phosphonomethylglycine are novel chemical compounds having desirable herbicidal activity.

10 Claims, No Drawings

N-THIOLCARBONYL DERIVATIVES OF N-PHOSPHONOMETHYLGLYCINE

This invention relates to a new class of organic chemical compounds. More particularly, this invention is concerned with novel derivatives of N-phosphonomethylglycine wherein a thiolcarbonyl group, RS(O)C—, is attached to the nitrogen atom. This class of compounds has been found to display desirable herbicidal activity when applied to certain varieties of weeds or undesired plants.

The compounds of the present invention may be represented by the structural formula

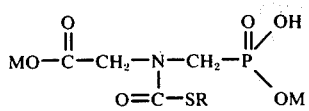

wherein R is lower alkyl, phenyl or benzyl. In addition to the unsubstituted rings, the phenyl or benzyl which represent R can have a chlorine, nitro, methoxy, methyl or trifluoromethyl group thereon. In said formula, each M represents hydrogen or a salt-forming cation which is alkali metal, ammonium or lower alkyl hydrocarbon amine. If only one M is hydrogen and the other is a cation, the cation would be expected to be attached at the phosphonic acid end of the molecule.

As employed herein, the term lower alkyl designates those alkyl radicals which contain up through six carbon atoms in a straight or branched chain. The compounds wherein M is one of the salt-forming cations defined above will be hereinafter referred to as the herbicidally acceptable salts of the parent compounds.

U.S. Pat. No. 3,799,758 describes the preparation of N-phosphonomethylglycine and certain of its esters, amides and salts. This patent also describes the use of such compounds as contact or post-emergent herbicides. The novel compounds of the present invention are prepared by first making a dibasic salt of N-phosphonomethylglycine, e.g., disodium salt. Said salt is then reacted with a chlorothiolformate in the presence of sodium hydroxide. The mixture can be checked with a few drops of phenolphthalein during the reaction, and additional alkali can be added to prevent said mixture from becoming acidic. The product obtained is in the form of a dibasic salt of the above formula. Such product can thereafter be acidified to a monobasic salt of said formula, or to a free acid, in the conventional manner. The reaction of the glycine and the thiolformate is most conveniently carried out at room temperatures or below.

The following illustrative, non-limiting examples will serve to further demonstrate to those skilled in the art the manner in which specific compounds within the scope of the invention can be prepared.

EXAMPLE I

A suitable reaction vessel is charged with 16.9 grams (0.10 mole) of N-phosphonomethylglycine in 30 ml. of water, and this is followed by the addition of 16.0 grams (0.20 mole) of 50% aqueous sodium hydroxide. The mixture is stirred and cooled to 20° C., after which there is added 12.5 grams of ethyl thiolchloroformate. Stirring is continued, and additional sodium hydroxide plus 1.5 grams of ethyl thiolchloroformate are added. The product is dried to yield a hard pink solid. Said product is then dissolved in water, filtered, acidified with HCl, and allowed to crystallize. There is obtained the mono-sodium salt of N-ethylthiolcarbonyl-N-phosphonomethylglycine (as the dihydrate), m.p. 240°–245° C. (dec.). Element 1 analysis shows 9.40% phosphorous and 9.99% sulfur as against calculated values of 9.83% and 10.17% for the dihydrate, $C_6H_{15}NNaO_8PS$.

EXAMPLE II

A suitable reaction vessel is charged with 16.9 grams of N-phosphonomethylglycine in 30 ml. of water, and this is followed by the addition of 16.0 grams of 50% aqueous sodium hydroxide. The mixture is stirred at about 15° C. while 17.3 grams of phenyl thiolchloroformate is added rapidly. Stirring is continued, and another 2.0 grams of the thiolchloroformate is added. The resultant slurry is acidified with HCl to precipitate a crystalline solid. This solid is dissolved in water and extracted with ether to remove an odorous oil. The material is then reprecipitated with HCl, rinsed well with water, and dried to yield the mono-sodium salt of N-phenylthiolcarbonyl-N-phosphonomethylglycine, m.p. 250°–260° (sint.), as a white powder. Elemental analysis gives 10.30% sulfur and 9.70% phosphorous as against calculated values of 9.80% and 9.47% for $C_{10}H_{11}NNaO_6PS$.

Further acidification of this product, or the product of Example I, yields the corresponding N-thiolcarbonyl-N-phosphonomethylglycine.

EXAMPLE III

Following the procedures described in detail in the above examples, substitution of other thiolchloroformates in the reaction produce the products indicated below. Although such products are named in their free acid form, it will be understood that the herbicidally effective mono and dibasic salts of this invention are so readily prepared. The specific salts are determined by the material employed to neutralize the N-phosphonomethylglycine at the start of the reaction, or, alternatively, an acid product of this invention can be neutralized after preparation. The number of salt-forming cations is determined by the extent to which a product is finally acidified with HCl.

Using benzyl thiolchloroformate in the above procedures, the product obtained is N-benzylthiolcarbonyl-N-phosphonomethylglycine. Using p-chlorophenyl thiolchloroformate in said procedures, the product obtained is N-p-chlorophenylthiolcarbonyl-N-phosphonomethylglycine. Similarly, using m-tolyl thiolchloroformate in said procedures, the product obtained is N-m-tolylthiolcarbonyl-N-phosphonomethylglycine.

EXAMPLE IV

N-phosphonomethylglycine is reacted with 50% sodium hydroxide as described above to prepare an aqueous solution of the disodium salt of said glycine. To a 31.5 gram portion of this solution is added 7.0 grams of isopropyl thiolchloroformate. The mixture is cooled at about 15° C., and several portions of sodium hydroxide are added, followed by another 1.0 gram of the thiolchloroformate. The resultant solution is extracted with ether and benzene to remove oils, after which the aqueous layer is acidified with HCl. A crystalline solid forms on standing, and it is collected and redissolved in water. This solution is concentrated to a crystalline product, filtered, washed twice with water, and dried. The product, obtained as a white powder, is the mono-sodium salt of N-isopropylthiolcarbonyl-N-phosphonomethylglycine, m.p. 250°–253° C. (dec.). Elemental analysis gives 11.25% sulfur and 10.76% phosphorous as against calculated values of 10.94% and 10.56% for $C_7H_{13}N$ $NaO_6PS$.

EXAMPLE V

To a 31.5 gram portion of a solution of disodium salt of N-phosphonomethylglycine, prepared as above, is added 8.0 grams of n-butyl thiolchloroformate. The mixture is stirred at about 20° C., and portions of sodium hydroxide are added, followed by an additional 1.0 gram of the thiolchloroformate. The mixture is extracted with ether and benzene, and an aqueous layer is then acidified with HCl. Crystals which form slowly are filtered, washed with water and dried. This product is redissolved in water, filtered, concentrated, washed and dried. The product, obtained as a white powder, is the mono-sodium salt of N-n-butylthiolcarbonyl-N-phosphonomethylglycine, m.p. 245°–250° C. (dec.). Elemental analysis show 10.68% sulfur and 10.25% phosphorous as against calculated values of 10.44% and 10.08% for $C_8H_{15}NNaO_6PS$.

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergence herbicidal activity index used in Table I and II is as follows:

| Plant Response | Index |
|---|---|
| 0–24% Killed | 0 |
| 25–49% Killed | 1 |
| 50–74% Killed | 2 |
| 75–99% Killed | 3 |
| All Killed | 4 |

In said Tables, WAT indicates weeks after treatment, and the plant species treated are each represented by a code letter as follows:

A - Canada Thistle
B - Cocklebur
C - Velvet Leaf
D - Morning Glory
E - Lambsquarter
F - Smartweed
G - Nutsedge
H - Quackgrass
I - Johnson Grass
J - Downy Brome
K - Barnyard Grass
L - Soybean
M - Sugar Beet
N - Wheat
O - Rice
P - Sorghum
Q - Wild Buckwheat
R - *Hemp Sesbania*
S - Panicum Spp
T - Crabgrass

TABLE I

| Compound of Example | WAT | kg/h | A | B | C | D | E | F | G | H | I | J | K |
|---|---|---|---|---|---|---|---|---|---|---|---|---|---|
| I | 2 | 11.2 | — | 1 | 1 | — | 4 | 2 | 1 | 1 | 1 | 1 | 3 |
|   | 4 | 11.2 | — | 2 | 2 | — | 4 | 3 | 0 | 2 | 1 | 1 | 3 |
| II | 2 | 11.2 | 2 | 1 | 1 | 2 | 3 | 2 | 2 | 1 | 1 | 1 | 3 |
|   | 4 | 11.2 | 2 | 2 | 2 | 3 | 4 | 3 | 2 | 3 | 2 | 3 | 3 |
|   | 2 | 4.48 | 2 | 2 | 2 | 2 | 2 | 2 | 2 | 2 | 1 | 1 | 2 |
|   | 4 | 4.48 | 2 | 2 | 2 | 2 | 3 | 1 | 2 | 2 | 2 | 1 | 2 |
| IV | 2 | 11.2 | 0 | 1 | 0 | 1 | 3 | 3 | 1 | 0 | 1 | 0 | 2 |
|   | 4 | 11.2 | 0 | 1 | 0 | 1 | 3 | 3 | 1 | 1 | 0 | 1 | 2 |
| V | 2 | 11.2 | 1 | 1 | 1 | 1 | 1 | 3 | 1 | 0 | 1 | 0 | 1 |
|   | 4 | 11.2 | 1 | 2 | 0 | 1 | 1 | 3 | 1 | 0 | 0 | 0 | 1 |

TABLE II

| Compound of Example | WAT | kg/h | L | M | N | O | P | B | Q | D | R | E | F | C | J | S | K | T |
|---|---|---|---|---|---|---|---|---|---|---|---|---|---|---|---|---|---|---|
| I | 2 | 4.48 | 1 | 1 | 2 | 0 | 1 | 1 | 2 | 1 | 1 | 2 | 2 | 0 | 1 | 3 | 2 | 3 |
|   | 4 | 4.48 | 0 | 2 | 2 | 1 | 1 | 0 | 2 | 1 | 1 | 2 | 1 | 0 | 1 | 3 | 2 | 3 |
|   | 2 | 1.12 | 0 | 0 | 2 | 0 | 0 | 0 | 1 | 0 | 0 | 1 | 0 | 1 | 1 | 0 | 1 | 2 |
| II | 2 | 4.48 | 1 | 3 | 3 | 1 | 2 | 3 | 1 | 2 | 2 | 3 | 3 | 3 | 2 | 3 | 3 | 4 |
|   | 4 | 4.48 | 1 | 4 | 4 | 3 | 2 | 3 | 2 | 2 | 2 | 3 | 3 | 3 | 2 | 4 | 3 | 4 |
|   | 2 | 1.12 | 0 | 1 | 2 | 0 | 2 | 1 | 2 | 2 | 1 | 3 | 1 | 0 | 2 | 3 | 2 | 3 |
|   | 4 | 1.12 | 0 | 3 | 1 | 1 | 2 | 1 | 1 | 2 | 1 | 4 | 2 | 0 | 2 | 3 | 3 | 3 |
| IV | 2 | 4.48 | 0 | 1 | 1 | 0 | 1 | 0 | 1 | 1 | 0 | 1 | 0 | 1 | 0 | 1 | 1 | 2 |
|   | 4 | 4.48 | 0 | 1 | 0 | 0 | 0 | 0 | 1 | 0 | 2 | 1 | 0 | 1 | 3 | 1 | 3 |
|   | 2 | 1.12 | 0 | 0 | 0 | 0 | 0 | 0 | 0 | 0 | 0 | 0 | 0 | 0 | 0 | 0 | 0 | 2 |
|   | 2 | 0.28 | 0 | 0 | 0 | 0 | 0 | 0 | 0 | 0 | 0 | 0 | 0 | 0 | 0 | 0 | 0 | 1 |
| V | 2 | 5.6 | 0 | 0 | 1 | 0 | 1 | 0 | 0 | 1 | 0 | 2 | 2 | 0 | 0 | 2 | 2 | 3 |
|   | 4 | 5.6 | 0 | 0 | 0 | 0 | 0 | 0 | 0 | 1 | 0 | 1 | 4 | 0 | 1 | 2 | 2 | 3 |
|   | 2 | 1.12 | 0 | 0 | 0 | 0 | 0 | 0 | 0 | 0 | 0 | 1 | 0 | 0 | 0 | 0 | 0 | 2 |
|   | 2 | 0.28 | 0 | 0 | 0 | 0 | 0 | 0 | 0 | 1 | 0 | 0 | 0 | 0 | 0 | 1 | 1 | 2 |

It should be noted that the compound of Example II was also applied to the group of plants in Table II at rates of 0.22 and 0.11 kg/h, and a reading of 0 was observed on all species.

The phytotoxicant compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly where the active ingredient is water soluble.

The phytotoxicant compositions of this invention, particularly liquids, preferably contain as a conditioning agent one or more surface-active agents in amounts sufficient to render a given composition readily dispersible in water or in oil. The incorporation of a surface-active agent into the compositions greatly enhances their efficacy. By the term surface-active agent it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N(long chain acid) taurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible compositions of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert extender, all parts being by weight of the total composition. Where required, from about 0.1 to 2.0 parts by weight of the inert extender can be replaced by a corrosion inhibitor or antifoaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform and usually contains from 5 to about 95 parts by weight active ingredient, from about 0.25 to 25 parts by weight dispersant, and from about 4.5 to 94.5 parts by weight of water.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example fertilizers, phytotoxicants and plant growth regulators, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, itriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy)phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide 2',6'-diethyl-N-methoxymethyl-2-chloroacetanilide
monosodium acid methanearsonate
disodium methanearsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective amounts of the glycines are applied to above ground portions of plants. The application of liquid and particulate solid herbicidal compositions to above ground portions of plants can be carried out by conventional methods, e.g. power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.25 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:
1. A compound of the formula

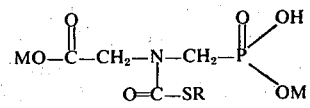

wherein each M is hydrogen alkali metal, ammonium or lower alkyl hydrocarbon amine, R is lower alkyl, phenyl or benzyl, and said phenyl or benzyl can contain a chlorine, nitro, methyl, methoxy or trifluoromethyl substituent.

2. A compound as defined in claim 1 wherein R is phenyl.
3. A compound as defined in claim 1 wherein R is benzyl.
4. A compound as defined in claim 1 wherein R is lower alkyl.
5. A compound as defined in claim 4 wherein said lower alkyl is methyl.
6. A compound as defined in claim 4 wherein said lower alkyl is ethyl.
7. A compound as defined in claim 4 wherein said lower alkyl is isopropyl.
8. A compound as defined in claim 4 wherein said lower alkyl is n-butyl.
9. A compound as defined in claim 1 wherein each M is hydrogen.
10. A compound of the formula

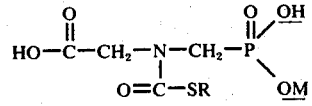

where R is lower alkyl, phenyl or benzyl, and said phenyl or benzyl can contain a chlorine, methyl, methoxy or trifluoromethyl substituent, and M is alkali metal, ammonium or lower alkyl hydrocarbon amine.

* * * * *